(12) United States Patent
Yacoubian

(10) Patent No.: US 7,495,369 B2
(45) Date of Patent: Feb. 24, 2009

(54) BROADBAND IMAGER

(76) Inventor: Araz Yacoubian, 2112 Vuelta Ct., Carlsbad, CA (US) 92009

( * ) Notice: Subject to any disclaimer, the term of this patent is extended or adjusted under 35 U.S.C. 154(b) by 272 days.

(21) Appl. No.: 11/442,406

(22) Filed: May 26, 2006

(65) Prior Publication Data
US 2007/0040469 A1   Feb. 22, 2007

Related U.S. Application Data

(60) Provisional application No. 60/685,236, filed on May 26, 2005.

(51) Int. Cl.
*H01L 41/08* (2006.01)
(52) U.S. Cl. .................. 310/311; 359/299; 310/364
(58) Field of Classification Search .......... 310/311, 310/334, 313 R
See application file for complete search history.

(56) References Cited

U.S. PATENT DOCUMENTS

| 4,025,954 A | * | 5/1977 | Bert ..................... 348/198 |
| 4,209,725 A | * | 6/1980 | Dieulesaint et al. ..... 310/313 R |
| 4,311,938 A | * | 1/1982 | Ballato et al. ............ 310/311 |
| 4,378,497 A | | 3/1983 | Giallorenzi |
| 4,524,294 A | * | 6/1985 | Brody ....................... 310/311 |
| 4,847,854 A | | 7/1989 | Van Dijk |
| 4,893,008 A | | 1/1990 | Horikawa |
| 5,285,261 A | | 2/1994 | Dumoulin |
| 5,447,845 A | * | 9/1995 | Chu et al. ..................... 435/6 |
| 6,292,682 B1 | | 9/2001 | Kruger |
| 6,490,470 B1 | | 12/2002 | Kruger |
| 6,504,289 B2 | | 1/2003 | Toda et al. |
| 6,633,774 B2 | | 10/2003 | Kruger |
| 6,662,040 B1 | | 12/2003 | Henrichs et al. |
| 6,728,024 B2 | * | 4/2004 | Ribak ........................ 359/299 |
| 6,848,295 B2 | | 2/2005 | Auner et al. |
| 2002/0097962 A1 | | 7/2002 | Yoshimura et al. |
| 2003/0012478 A1 | | 1/2003 | Pokrovski et al. |
| 2004/0220465 A1 | | 11/2004 | Cafarella |

FOREIGN PATENT DOCUMENTS

| EP | 0576104 A2 | 12/1993 |
| EP | 1051536 B1 | 7/2003 |
| WO | WO03/059168 A1 | 7/2003 |

* cited by examiner

*Primary Examiner*—Mark Budd
(74) *Attorney, Agent, or Firm*—Koestner Bertani LLP; Ken J. Koestner

(57) ABSTRACT

A sensor comprises a transducer substrate formed of a photo-acoustically sensitive material and having a receiving surface and an absorptive layer coupled to the transducer substrate receiving surface that detects broadband electromagnetic (EM) radiation.

40 Claims, 22 Drawing Sheets

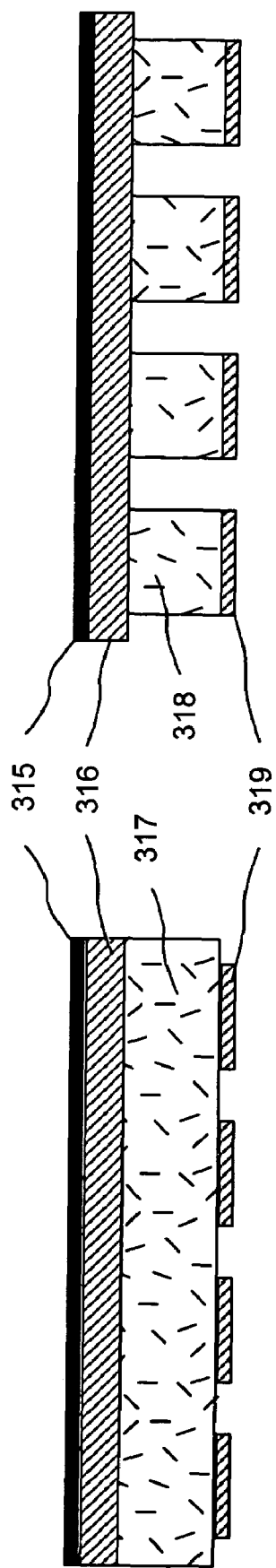

BROADBAND IMAGER

This application claims the benefit of priority to and incorporates herein by reference in its entirety for all purposes, U.S. Provisional Patent Application No. 60/685,236 entitled "BROAD BAND IMAGER," by Araz Yacoubian filed on May 26, 2005.

BACKGROUND OF THE INVENTION

Detection of broadband electromagnetic (EM) radiation such as visible, infrared, ultra-violet (UV) radiation, as well as radiation in other parts of the EM spectrum, has great interest in many technology areas. Many current technologies enable detection and imaging only in a narrow part of the EM spectrum, such as visible only, infra-red only, or UV.

Many conventional detection technologies utilize sensing of electronic transition between various states of atoms, excited by the incoming EM radiation, and are therefore limited to a narrow part of the EM spectrum. Technologies such as bolometers have a relatively broader response, but have slow response time.

SUMMARY OF THE INVENTION

In an illustrative embodiment, a sensor comprises a transducer substrate formed of a photo-acoustically sensitive material and having a receiving surface and an absorptive layer coupled to the transducer substrate receiving surface that detects broadband electromagnetic (EM) radiation.

BRIEF DESCRIPTION OF THE DRAWINGS

Embodiments of the invention relating to both structure and method of operation may best be understood by referring to the following description and accompanying drawings:

FIGS. 3A through 3D are multiple cross-sectional cutaway pictorial views showing embodiments of structures for spatial sampling of a broadband EM image;

DETAILED DESCRIPTION OF THE EMBODIMENTS

An ultra-broad band detector that covers a wide range of the electromagnetic (EM) spectrum is highly useful and desirable. Such a broadband detector or sensor that is also relatively fast is useful for imaging applications.

Various embodiments of a sensor and detection method are based on a photo-acoustic effect that can detect and image a broad-range of the electromagnetic spectrum simultaneously, at relatively high-speed suitable for imaging applications.

Figure 1:
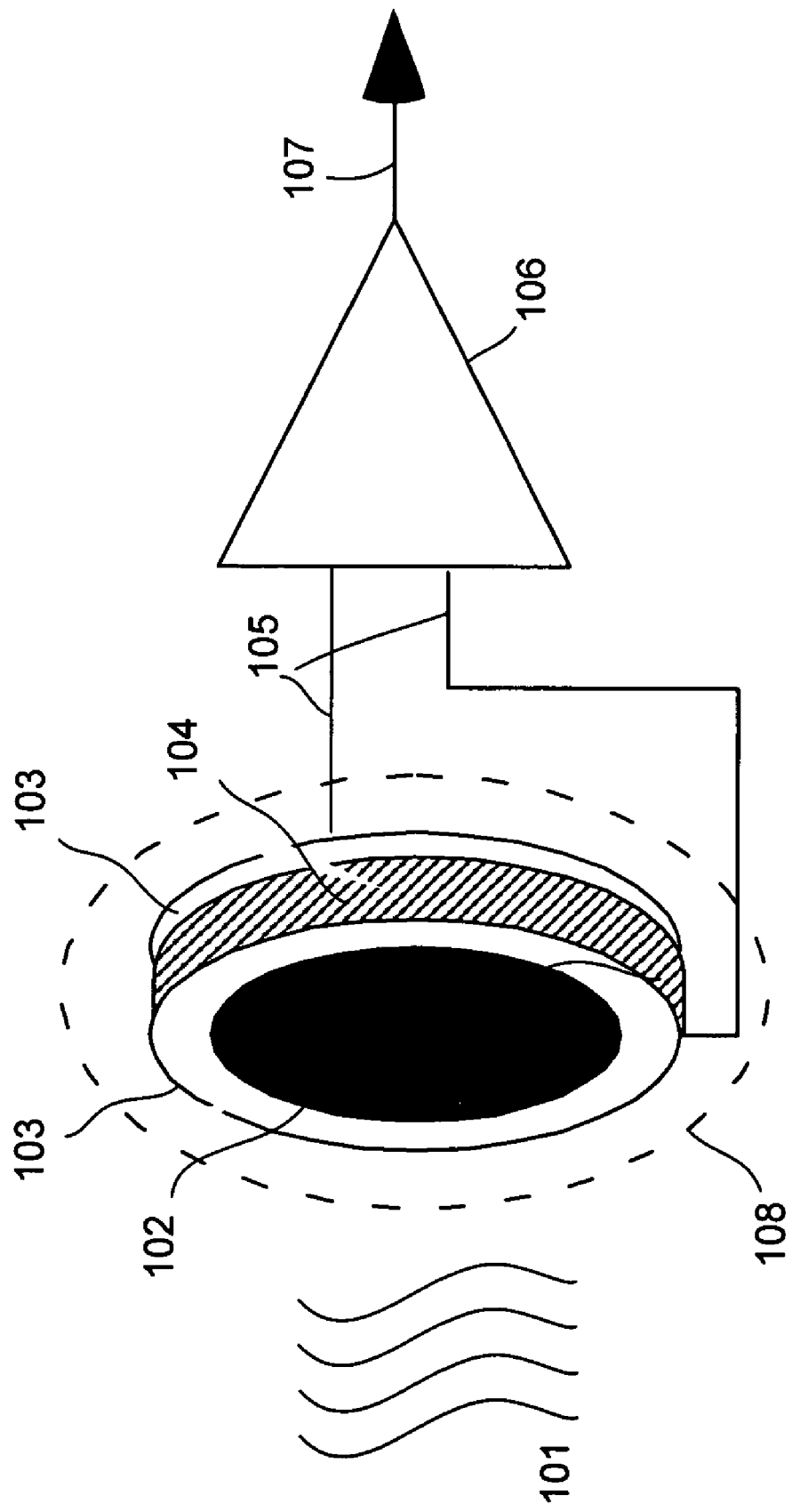
FIG. 1 is a perspective pictorial and block diagram illustrating an embodiment of a sensor configured for photo-acoustic detection of broadband electromagnetic radiation.

Referring to FIG. 1, a perspective pictorial and block diagram illustrates an embodiment of a sensor configured for photo-acoustic detection of broadband electromagnetic radiation and is useful in describing basic principles of the broadband detection scheme using photo-acoustic excitation. The illustrative broadband photo-acoustic detection apparatus is responsive to incident electromagnetic radiation 101 of arbitrary shape and direction, thus arbitrary phase and amplitude, and comprises a darkened surface 102, conductive layers 103, a photo-acoustically sensitive material 104, electrical connections 105, and a high-gain, low-noise amplifier 106. The detection apparatus or sensor generates an output signal 107 indicating presence of EM radiation. Conductive layers 103, the photo-acoustically sensitive material 104, and the coating 102 on the conductive layer constitute an electromagnetic radiation absorbing piezoelectric transducer 108 which can be called a sensor.

The sensor 108 detects electromagnetic radiation through a detection scheme based on photo-acoustic effect. In some embodiments, the sensor 108 is a piezoelectric transducer (PZT) comprising a piezoelectric material 104 sandwiched between two metallic or conductive surfaces or layers 103. The PZT 108 is connected to a high-gain, low noise amplifier 106. One surface, which may be called a receiving surface, of the PZT is coated with an absorptive layer 102. Any layer that absorbs incident radiation is suitable. For a broadband detection, a coating 102 is desirable that can absorb broadband radiation. One example of a suitable coating 102 is a thin layer of carbon.

In other embodiments, the sensor 108 can also be implemented using a capacitive approach, where the photo-acoustically sensitive material 104 is an insulator rather than piezoelectric material. Suitable insulators may be a vacuum, air, or other insulators.

When electromagnetic radiation is incident on the absorbing surface or layer 102, the absorbed electromagnetic energy is converted to a mechanical energy via the photo-acoustic effect, which is then converted to an electrical signal via the piezoelectric effect, or via a capacitive effect. The resulting electrical signal can be amplified via a high gain, low noise amplifier 106 to facilitate detection.

Because the detection method uses photo-acoustic effect, the technique can therefore be used to detect broadband electromagnetic radiation. The broadband spectrum can include, visible, infrared (IR), ultraviolet (UV) band, X-ray, microwave and higher frequencies, as long as the radiation is absorbed by the absorbing surface of the sensor. Even gamma rays can be detected with the sensor, for example by placing a material such as aluminum foil in front of the absorbing surface 102.

Accordingly, in various embodiments the sensor 108 comprises a photo-acoustically sensitive material 104 with absorbing layer 102 that detects broadband electromagnetic (EM) radiation. In some embodiments, the sensor 108 includes piezoelectric material as the photo-acoustically sensitive material. In other embodiments, the photo-acoustically sensitive material can be a capacitive material. A high-gain amplifier is useful to improve detection.

Figure 2A:
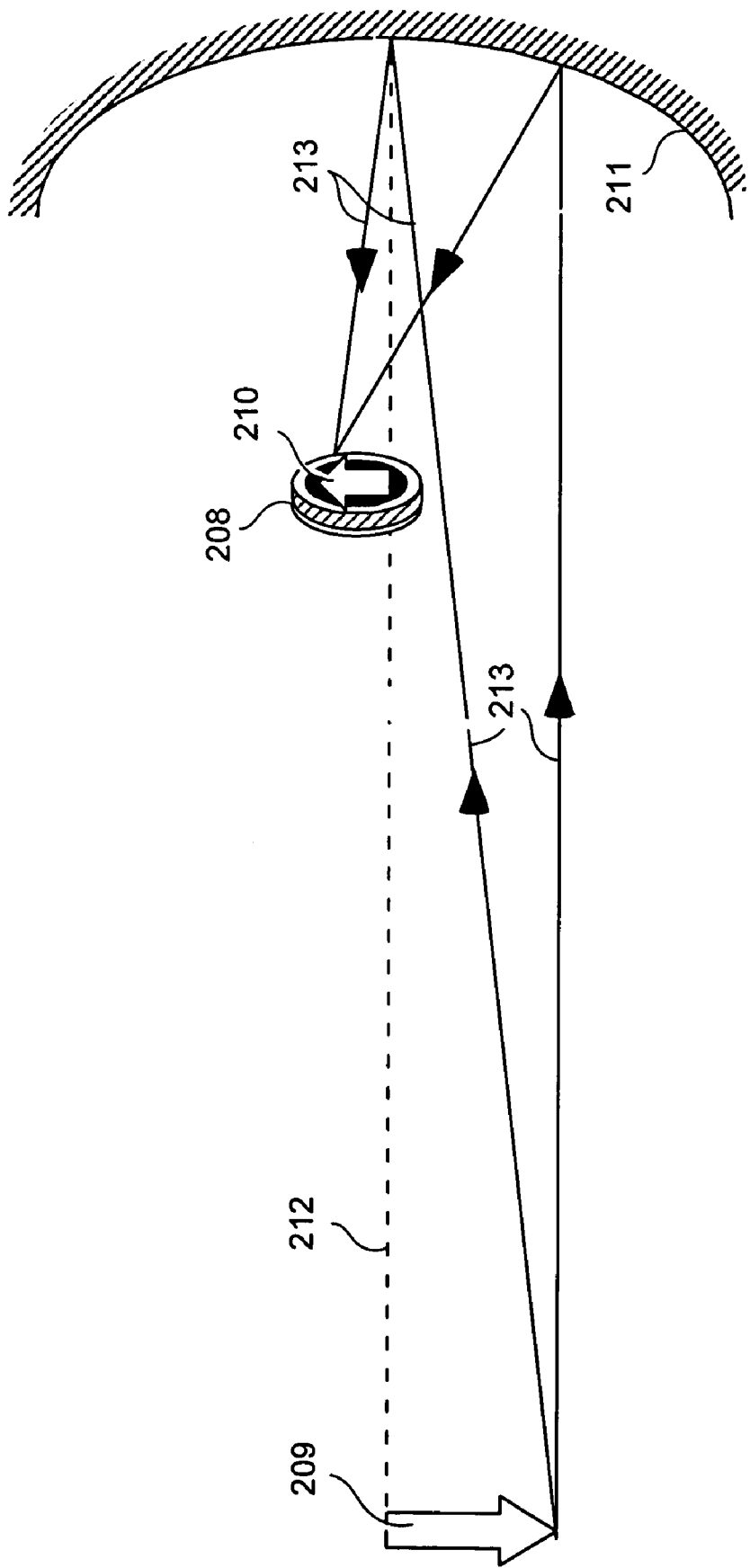
FIGS. 2A and 2B are pictorial diagrams that depict embodiments of arrangements for usage in photo-acoustic imaging of broadband electromagnetic radiation.
Figure 2B:
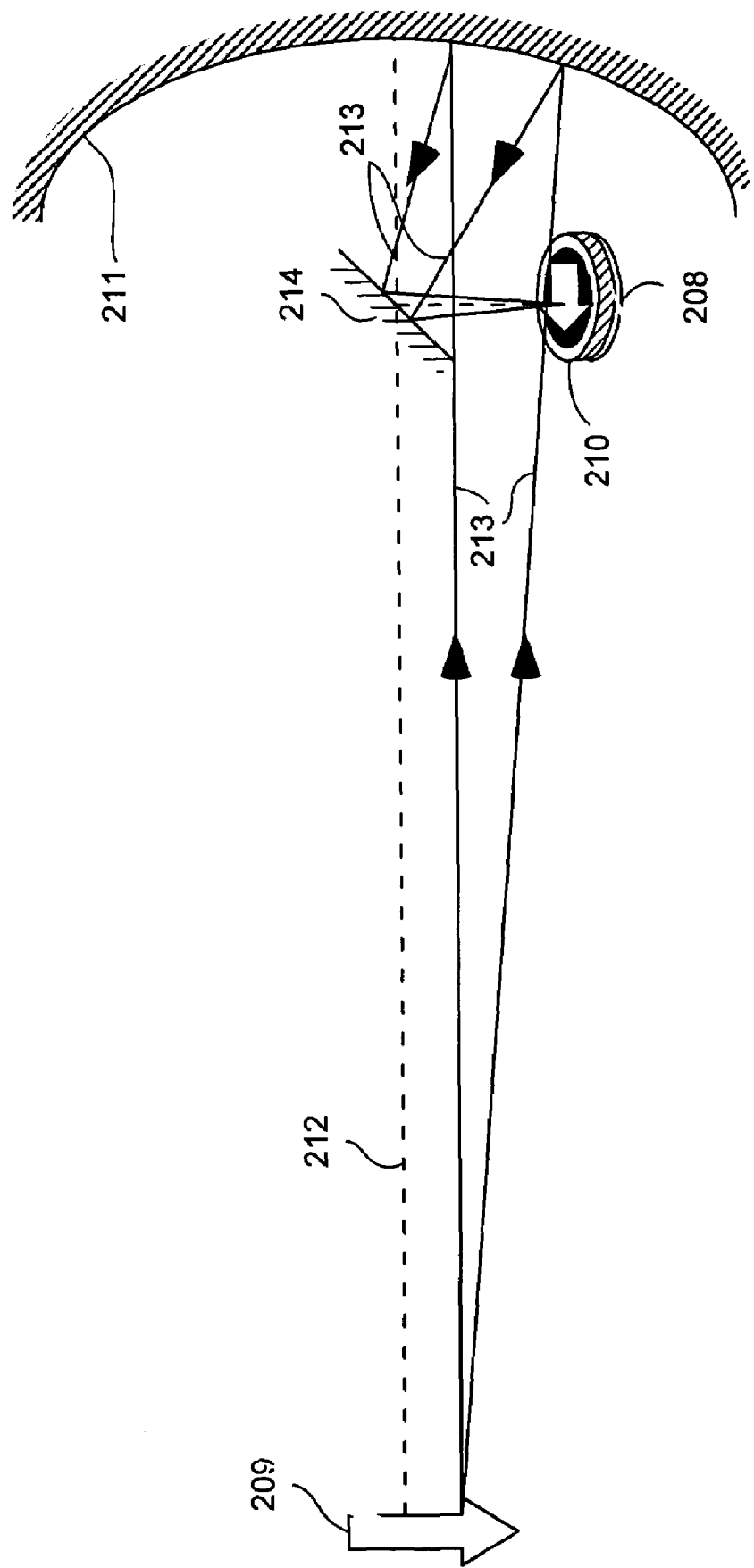

Referring to FIGS. 2A and 2B, pictorial diagrams depict embodiments of arrangements for usage in photo-acoustic imaging of broadband electromagnetic radiation. The photo-acoustic sensor 108 shown in FIG. 1 can be used to image the incident EM radiation. Incoming EM radiation can be imaged through usage of imaging optics and a spatial sampling scheme. Imaging can be achieved in a number of ways, such as using broadband EM band-specific refractive lenses, diffractive optics, or broadband reflective mirrors as shown in FIGS. 2A and 2B. For example, an imaging mirror can be used to image UV, visible and IR simultaneously.

Broadband EM radiation of an object 209 can be focused using reflective optics 211 with a sensor 208 placed in front of the mirror as shown in FIG. 2A, and sensor 208 placed at an angle with the image reflected using an intermediated broadband mirror 214 in FIG. 2B. A reflective surface 211 such as a broadband parabolic mirror images the object 209 onto the sensor 208, where an image 210 is formed. Optic axis 212 is depicted in dotted lines. Arrowed lines indicate optical ray 213 paths.

For astronomical applications, the sensor can simply be placed in the image plane, since the telescope will image the object onto the sensor. FIGS. 2A and 2B show a two-dimensional imaging apparatus. If a one-dimensional imaging is desired, such as a line scan, a cylindrical mirror can be used to focus the object in one dimension.

Referring to FIGS. 3A through 3D, several cross-sectional cut-away pictorial views show embodiments of structures for spatial sampling of a broadband EM image.

Spatial sampling can be achieved by various techniques including usage of a pixelated or multi-element sensor, a moving slit or iris in front of a single element sensor, by scanning a single element sensor, or other suitable method.

Figures 3C, 3D:
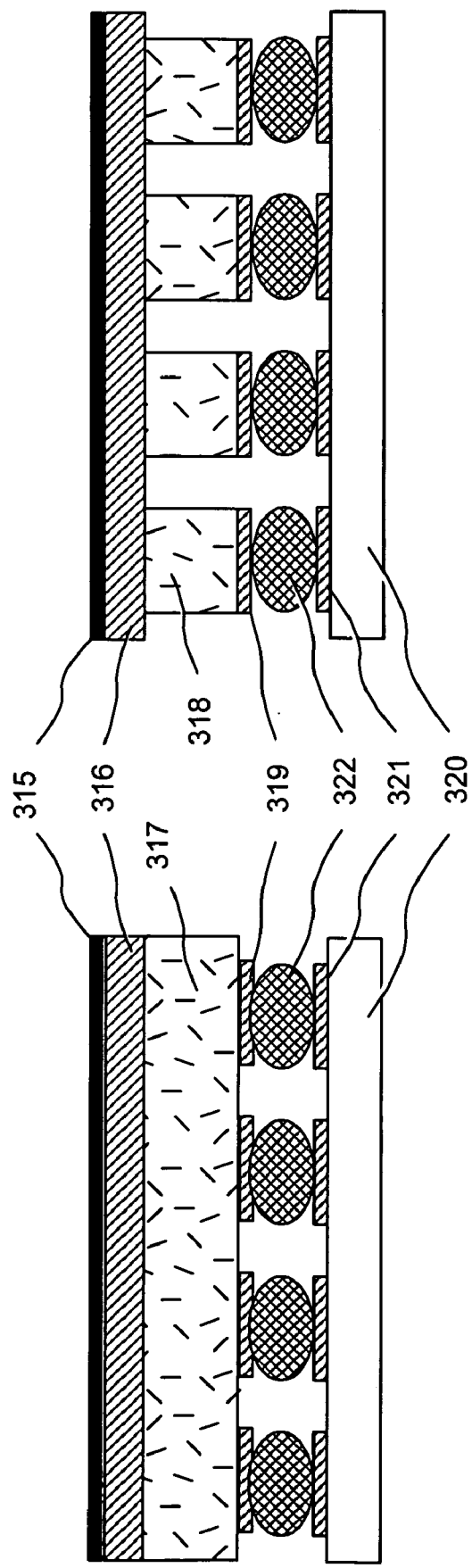

Images may be captured through a pixelated sensor scheme. The first scheme utilizes a pixelated piezoelectric transducer (PZT) or capacitive sensor. The cross-sections of two different pixelation scheme embodiments are shown in FIGS. 3A and 3B. Methods for extracting a signal from each of multiple pixels using a read-only integrated circuit (ROIC) is shown in FIGS. 3C and 3D.

A pixelation scheme for a photo-acoustic sensor is shown in FIG. 3A. Only a back conductor 319 is pixelated. In FIG. 3B, both a conductor 319 and piezoelectric material 318 are pixelated. The devices contain an absorbing layer 315, a conductor 316 such as a brass layer), piezoelectric material 317 in unpatterned form, or in the case of a capacitive detection technique the piezoelectric material can be replaced by a dielectric insulator or air. The configuration shown in FIG. 3B contains a patterned piezoelectric material 318, or dielectric material or air if a capacitive detection is used. The back side is coated with conductors 319.

The pixelated sensor can be connected to a read only integrated circuit (ROIC) as shown in FIGS. 3C and 3D with ROIC 320 and ROIC connectors 321 using solder bumps/electrical conductor 322.

The pixelation method shown in FIGS. 3A and 3B can be implemented either mechanically such as by micro-machining using diamond cutting or dicing, or lithographically. For a lithographic technique, the PZT device can be spin coated with a photo-resist, pixels patterned using a mask aligner, and electrodes etched using metal etching, and the PZT material. For the architecture shown in FIG. 3B, or for a dielectric material if a capacitive method is used, materials can be etched using ion milling or reactive ion etching.

The illustrative pixelation methods and structures shown in FIGS. 3A and 3B can be implemented for a sensor constructed from any suitable photo-acoustically sensitive material including piezoelectric materials and capacitive materials. Similarly, the structures and associated methods shown in FIGS. 3C and 3D enabling extraction of a signal from pixelated sensors using read-only integrated circuits (ROICs) can be implemented for sensors constructed from any suitable photo-acoustically sensitive material including piezoelectric materials and capacitive materials. The sensors can be used in any suitable arrangement for imaging incident EM radiation.

Figure 4:
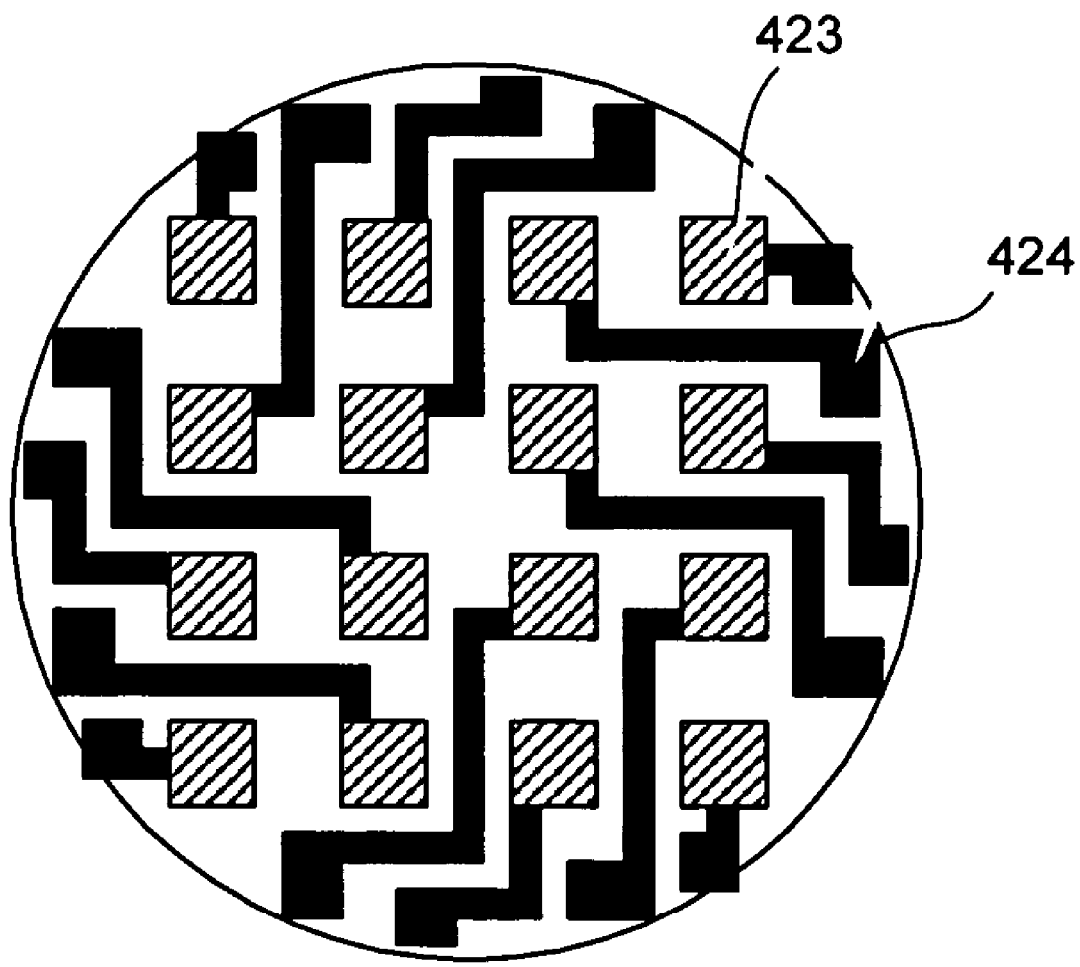
FIG. 4 is a schematic pictorial diagram illustrating an embodiment of a sensor structure and associated method that enable acquiring signals directly from a sensor by patterning electrodes that connect to the individual pixels.

Referring to FIG. 4, a schematic pictorial diagram illustrates an embodiment of a sensor structure and associated method that enable acquiring signals directly from a sensor, rather than by using an ROIC, by patterning electrodes that connect to the individual pixels. The illustrative example shows a pixelated sensor with electrodes 424 included to extract a signal using photo-acoustically active pixels 423 patterned, for example as shown in FIG. 3A or 3B, and electrodes 424 to extract the photo-acoustic signal. In other implementations or embodiments, a sensor can be bump-bonded to an ROIC, and electrodes to extract the parallel signal output will not be necessary.

FIG. 4 depicts a 4×4 pixelation scheme, but can be expanded to N×N pixels using the same approach, where N is an arbitrary number. For very large number N arrays, the lines can interfere with the pixels. To avoid interference but still obtain N×N parallel output lines, a printed circuit with bumps on one side can be bump-bonded to the pixelated sensor that does not contain the electrodes, and the electrodes are printed on the opposing side of the printed circuit board. The lines and bumps on opposing sides of the printed circuit board can be connected through vias.

Spatial sampling can also be performed using a clocking circuit. FIG. 4 shows a pixelated architecture with parallel N×N output lines. For very large number of pixels, to avoid interconnection difficulties, conversion of the detected spatial signal to a serial output may be desired. The conversion can be attained using a clocking circuit. Each pixel output can be connected to a transistor network. Each transistor is activated with a clock signal, and a serial output signal contains a clocked signal in which individual pulse amplitudes correspond to a specific pixel value. A pixelated sensor can be combined to a transistor/amplifier network circuit using bump-bonding technique, enabling construction of a sensor with a very large number of pixels. The pixelated sensor can be bump-bonded to a read only integrated circuit (ROIC) that generates a clocked signal. The bump-bonding approach is depicted in FIGS. 3A through 3D.

The structure and associated method shown in FIG. 4 enabling direct reading from the sensor can be implemented for sensors constructed from any suitable photo-acoustically sensitive material including piezoelectric materials and capacitive materials. The sensors can be used in any suitable arrangement for imaging incident EM radiation.

Figure 5A:
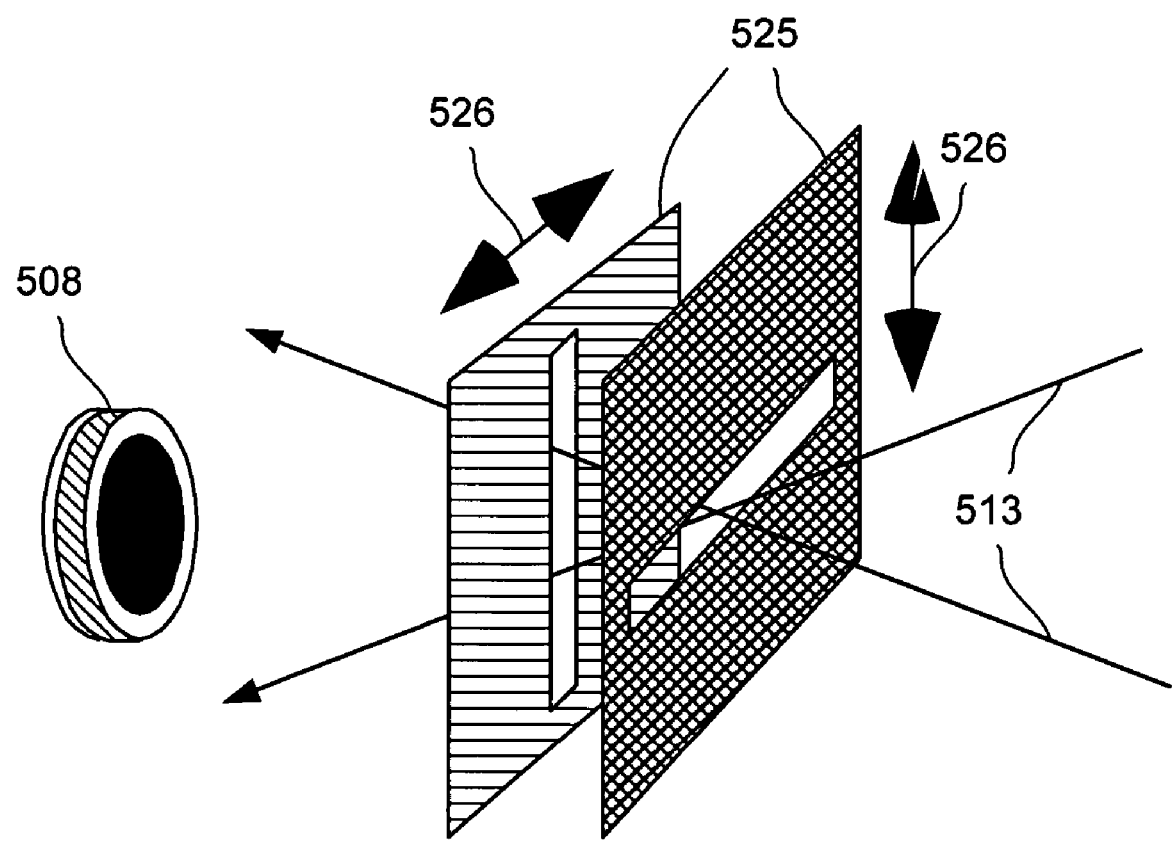
FIGS. 5A and 5B are perspective pictorial views showing embodiments of structures and methods for spatial sampling using scanning slits or a single iris or pinhole.
Figure 5B:
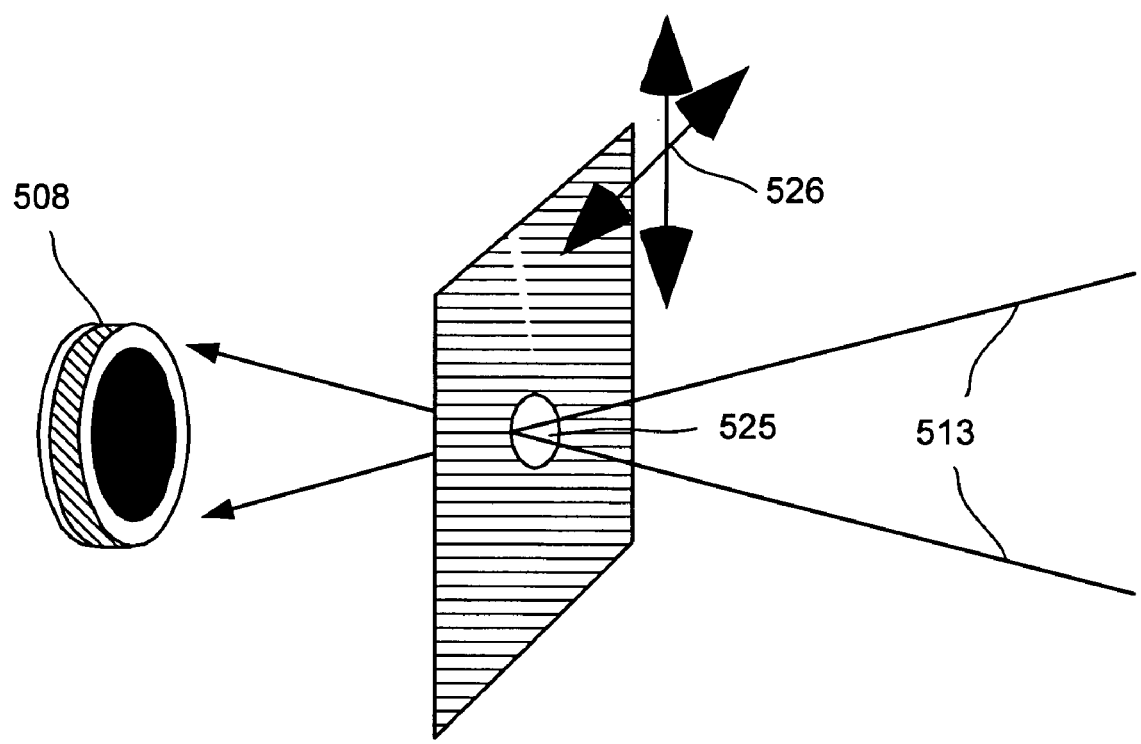

Referring to FIGS. 5A and 5B, perspective pictorial views show embodiments of structures and methods for spatial sampling using scanning slits or a single iris or pinhole. Another spatial sampling method involves use of a pair of diaphragms with scanning slits or a diaphragm with an aperture formed as a single iris or pinhole to sample the incident radiation pattern in the x and y directions in directions normal to the optic axis, as shown in FIGS. 5A and 5B.

Spatial sampling is attained by moving the slits or iris. Slits, pinhole or iris 525 form an aperture in one or more diaphragms placed either at the focus of the EM field, or placed directly against the single element photo-acoustic sensor 508. Slits or the iris move in both horizontal and vertical axes 526 in directions normal to the optic axis. Two methods of spatial scanning are shown including usage of two slits 525, shown in FIG. 5A, one scanned in horizontal direction, and the other in vertical direction. FIG. 5B illustrates usage of a single iris or pinhole 525 that is scanned both in horizontal and vertical directions.

In the architectures shown in FIGS. 5A and 5B, data is collected either continuously or after each scan. To obtain a better signal-to-noise ratio, after each scan the PZT can be activated either by turning on the amplifier, or by turning on a shutter in front of the detector. The data is then stored, and displaced on a monitor, for example a computer monitor, after the x,y scan is complete with corresponding coordinates.

The structures and associated methods shown in FIGS. 5A and 5B enabling spatial sampling using scanning slits or a single iris or pinhole can be implemented for sensors constructed from any suitable photo-acoustically sensitive material including piezoelectric materials and capacitive materials. The sensors can be used in any suitable arrangement for imaging incident EM radiation.

Figures 6A, 6B:
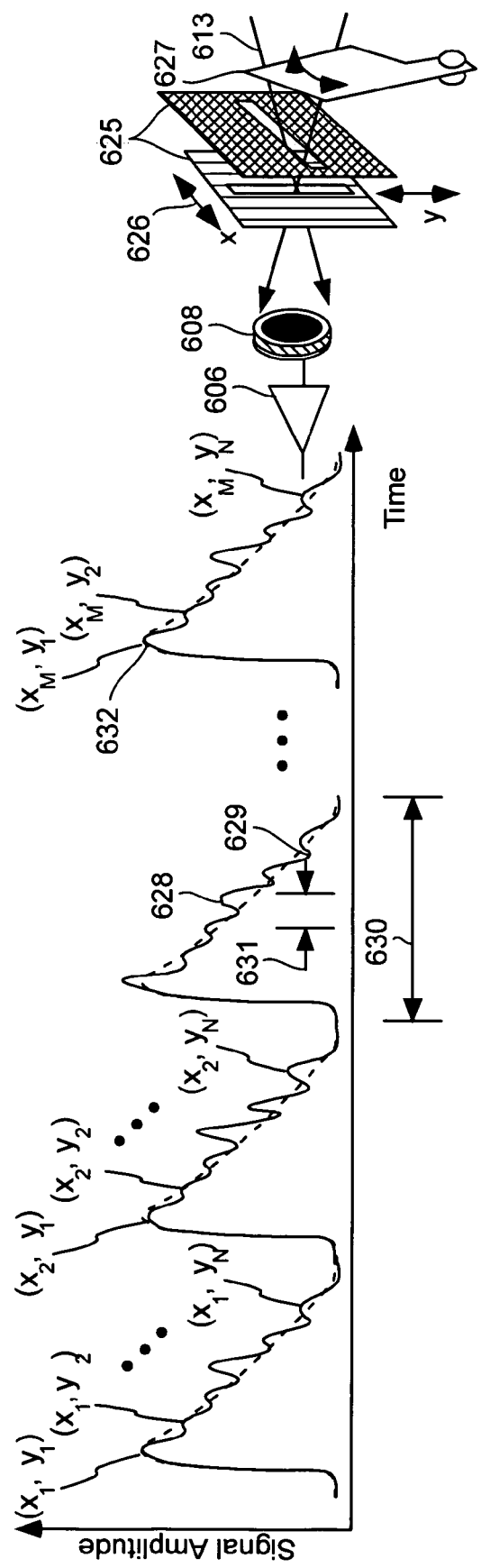
FIGS. 6A and 6B are a graph and a perspective pictorial view respectively illustrating an operation of scanning by continuous moving slits.

Referring to FIGS. 6A and 6B, a graph and perspective pictorial view respectively illustrate an operation of scanning by continuous moving slits. Another alternative for spatial sampling is a scanning system that performs continuous scanning of diaphragms with x and y slits that are moved at selected independent rates that can be different rates. An optional shutter can be used to block/pass the incoming radiation. The resulting signal has a saw-tooth like signal depicted in FIG. 6A, where each cycle corresponds to a single line scan in y direction for a given x position. The beginning of the sawtooth wave is generally the arrival of the horizontal (x) slit, and the initial fast response of the PZT. The full scanned data is analyzed to yield an incident EM radiation spatial distribution.

In the operation of scanning by continuous moving slits, a shutter 627 is used to block and pass EM radiation. The graph in FIG. 6B shows the amplified sensor output, where the solid line 628 is the amplified signal modulated due to spatial variation of the incident electromagnetic field 613. The dashed line 629 is the signal if EM field is spatially uniform. Difference between lines 628 and 629 is proportional to spatial distribution of the EM signal. Within each scan time 630, the x moving slit is held in one position, and the y moving slit is moved from position 1 to M, at a specific time interval 631. The y slit is then moved one step and the x slit is scanned again. The scheme is continued until the entire image area is scanned. The collected data is then converted to corresponding spatial coordinates 632.

FIG. 6B shows a mechanical shutter 627 that blocks and enables light to pass in on and off phases. In conditions or instances that are prohibitive of mechanical movement, the shutter 627 can be replaced by an electronic shutter, such as a liquid crystal light valve or a micro-electro-mechanical systems (MEMS) based light deflection used in a shutter mode, or any other mechanical, optical or electronic shutter. In case an artificial electromagnetic (EM) source is used to illuminate the object, the EM source can be turned on and off rather than using a shutter to pass or block incident electromagnetic radiation.

The structures and associated methods shown in FIGS. 6A and 6B enabling scanning by continuous moving slits to produce signals such as those shown in FIG. 6A can be implemented for sensors constructed from any suitable photo-acoustically sensitive material including piezoelectric materials and capacitive materials. The structures and associated methods shown in FIGS. 6A and 6B enabling scanning by continuous moving slits in combination with an electronic or mechanical shutter to produce signals such as those shown in FIG. 6A can be implemented for sensors constructed from any suitable photo-acoustically sensitive material including piezoelectric materials and capacitive materials. The sensors can be used in any suitable arrangement for imaging incident EM radiation.

FIGS. 5A, 5B, 6A, and 6B show various embodiments of devices to perform EM radiation imaging using a single element sensor scanned in horizontal and vertical directions.

Figure 7:
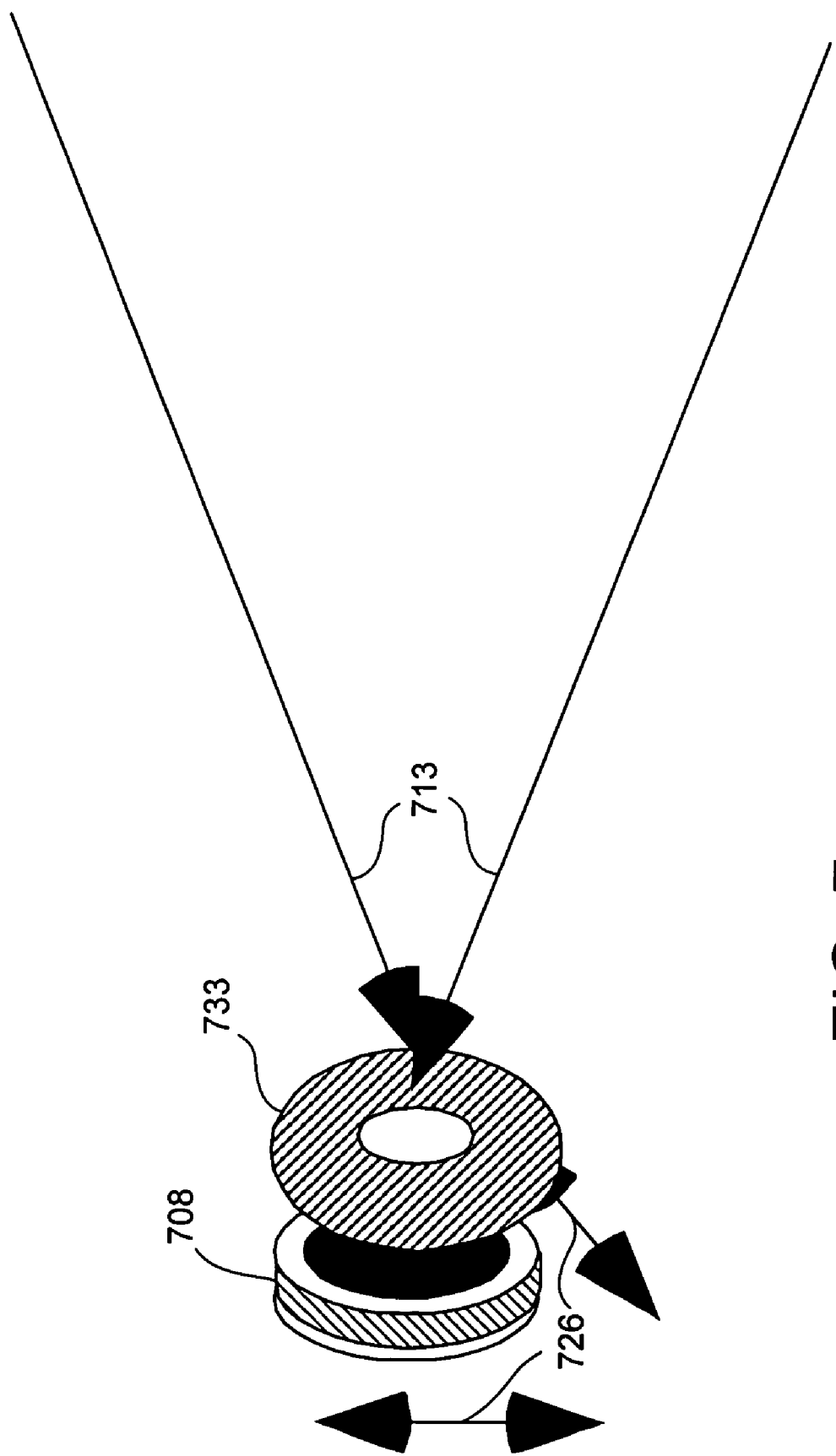
FIG. 7 is a perspective pictorial diagram showing a sensor in a configuration that enables spatial sampling by scanning a detector head.

Referring to FIG. 7, a perspective pictorial diagram illustrates a sensor in a configuration that enables spatial sampling by scanning a detector head. A third method of spatial sampling is performed by moving a single element sensor in the x and y directions, as depicted in FIG. 7. A diaphragm with a small pinhole 733 may be inserted in front of the sensor 708 and moved relative to the sensor 708 for increased spatial resolution. An optional shutter (not shown) can also be used with the pinhole scanning scheme.

Imaging is performed by moving a single element sensor 708 placed in the path of the EM radiation. An optional iris or pinhole 733 is used to attain high-spatial resolution.

To detect only narrow part of the EM spectrum, an appropriate filter can be placed in front of the sensor 708. For example, to detect in an IR-only spectrum, a double sided polished silicon (Si) plate can be placed that passes radiation above approximately 1 micron, while blocking the visible and UV EM radiation.

Various other imaging structures and methods can be used that incorporate the broadband sensor. For example, FIGS. 2A and 2B showed use of reflective optical elements to focus light onto the sensor. Other components can also be used to image an object onto the sensor which is depicted hereinafter in FIGS. 8, 9A, and 9B. The various imaging techniques can be combined with pixelated sensor methods or the scanning slit, pinhole or scanning sensor techniques depicted in FIGS. 3 through 7 to produce a broadband image.

Figure 8:
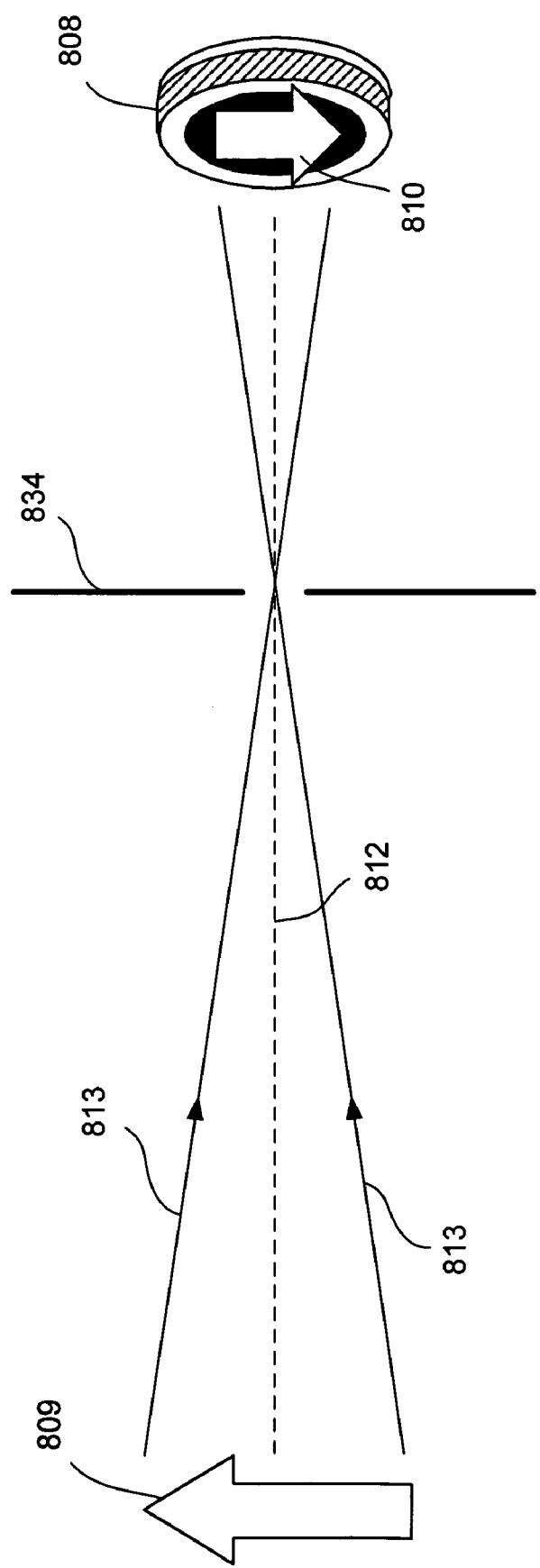
FIG. 8 is a pictorial view that shows an embodiment of a sensor arrangement configured for pinhole imaging.

Referring to FIG. 8, a pictorial view shows an embodiment of a sensor arrangement configured for pinhole imaging. One possible method to obtain a broadband image includes usage of a diaphragm intersected by an aperture in the form of a pinhole 834 for imaging. Operation is analogous to a pinhole camera. Pinhole imaging does not block any particular portion of the EM radiation and is therefore suitable for broadband imaging.

In broadband imaging using the pinhole approach, an imaged object 809 generates an incident electromagnetic field 813 by reflection, transmission, or emission along an optic axis 812. Illumination passes through the pinhole 834 to the sensor 808 to form image 810.

FIG. 8 shows a two-dimensional imaging apparatus. If a one-dimensional imaging is desired, such as a line scan, a slit can be used instead of pinhole to focus the object in one dimension.

Figure 9A:
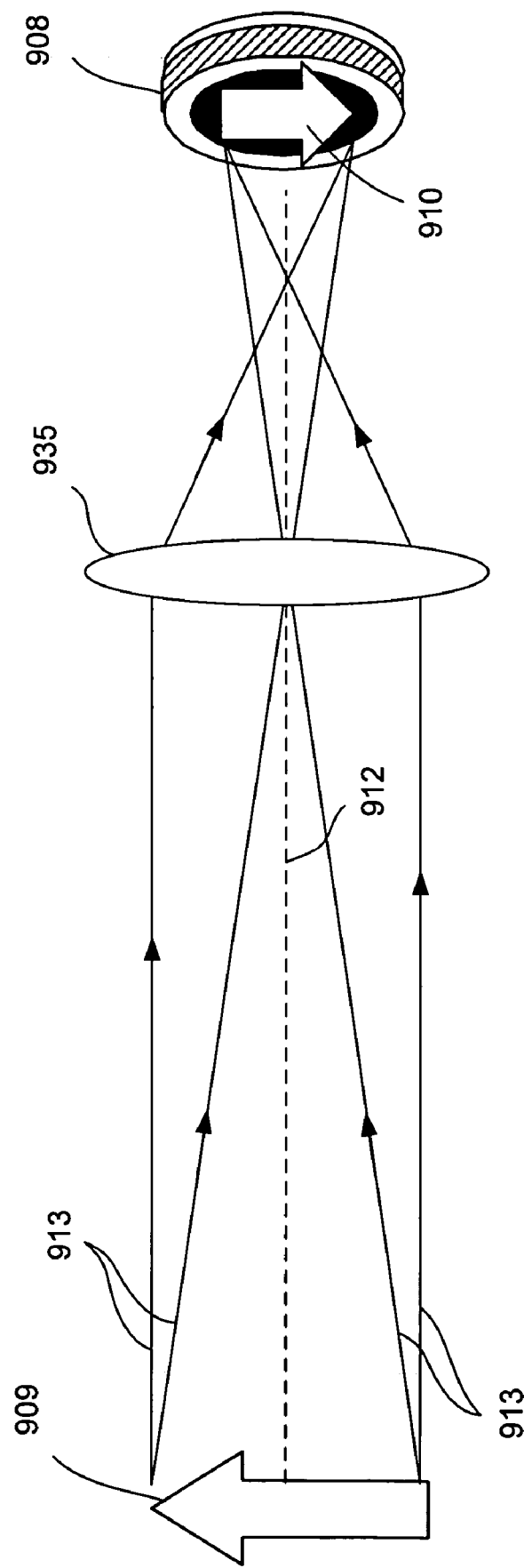
FIGS. 9A and 9B are perspective pictorial diagrams illustrating configurations using a sensor for imaging using specialty lenses, Fresnel lenses, and diffractive and holographic optical elements.
Figure 9B:
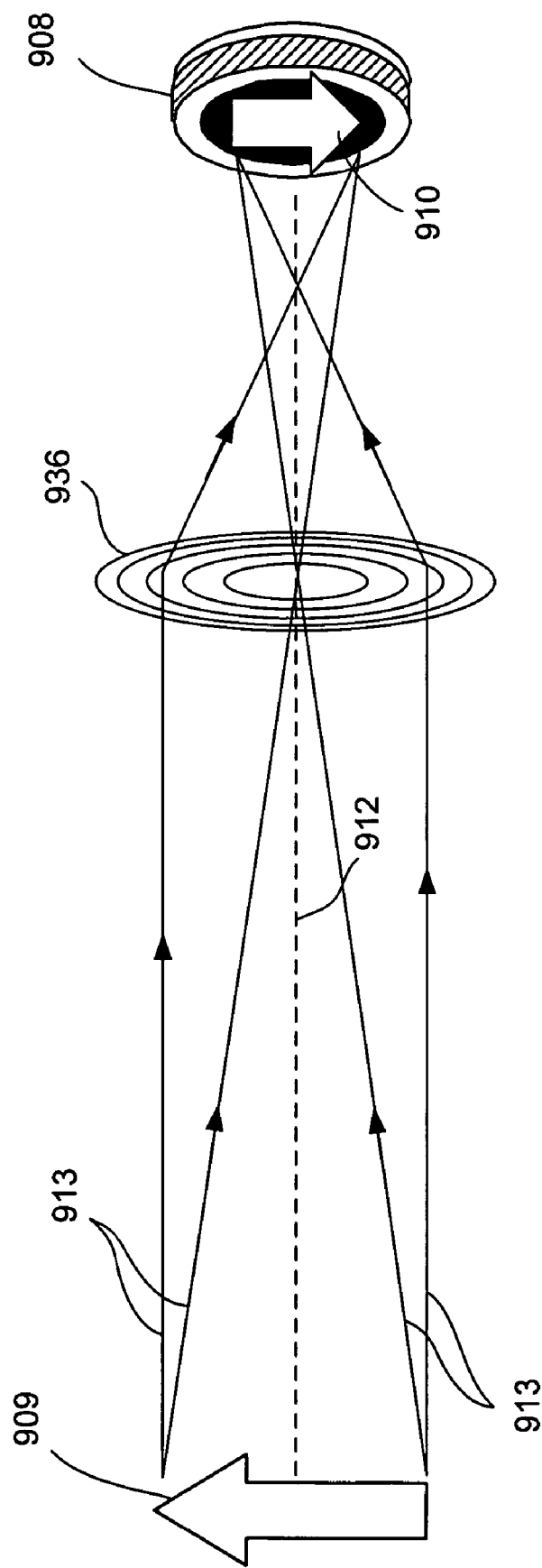

Referring to FIGS. 9A and 9B, perspective pictorial diagrams illustrate configurations using a sensor for imaging using specialty lenses, Fresnel lenses, and diffractive and holographic optical elements.

One drawback of the pinhole imaging depicted in FIG. 8 is blockage of a large portion of the incident EM field. To increase collection efficiency, a system can use a lens 935, for example a specialty material lens, as shown in FIG. 9A. The choice of the lens material depends on the EM radiation wavelength range of interest. In various arrangements and embodiments, a Fresnel lens, a diffractive optical element or a holographic optical element 936 can be used to image the incoming EM radiation as shown in FIG. 9B.

An imaged object 909 generates an incident electromagnetic field 913 by reflection, transmission, or emission along an optic axis 912. Illumination passes through the various lenses 935 and 936 to the sensor 908 to form image 910. FIGS. 9A and 9B show a two-dimensional imaging apparatus. If one-dimensional imaging is desired, such as a line scan, a cylindrical lens, a cylindrical Fresnel lens, or a cylindrical diffractive or holographic optical element can be used to focus the object in one dimension. If the Fresnel or diffractive lens 936 is replaced with a reflective Fresnel lens such as a mirror coated ruled lens, a grazing incident focusing optics or a diffractive or a holographic reflective optical element, then the detection scheme operates in reflection mode. Reflection mode imaging is useful for deep UV or x-ray imaging where grazing incident optics are more suitable for focusing the incident radiation than transmission optics.

Various structures and configurations can be implemented for noise reduction. The sensor shown in FIG. 1 can be sensitive to electric and acoustic noise. To reduce electrical noise, the PZT and amplifier can be electrically shielded. Such shielding is achieved by placing the amplifier and the PZT in a metallic housing, and connecting the ground of the amplifier and one of the electrodes to the housing. Ideally, the PZT and the amplifier can be contained in the same metal housing. The PZT is typically also sensitive to acoustic noise. Therefore the sensor can be acoustically shielded, which can be achieved by using foam absorbers around the PZT for sensor use in a noisy environment. Mechanical vibration also generates noise. To reduce mechanical noise, the PZT can be isolated using air cushions similar to the ones used in mechanically isolated optical tables. In addition, electrical filters such as low-pass, band-pass, or high-pass filters can be inserted following the amplifier to reduce or eliminate certain type of electrical and acoustic noise that have known frequency response.

Figure 10:
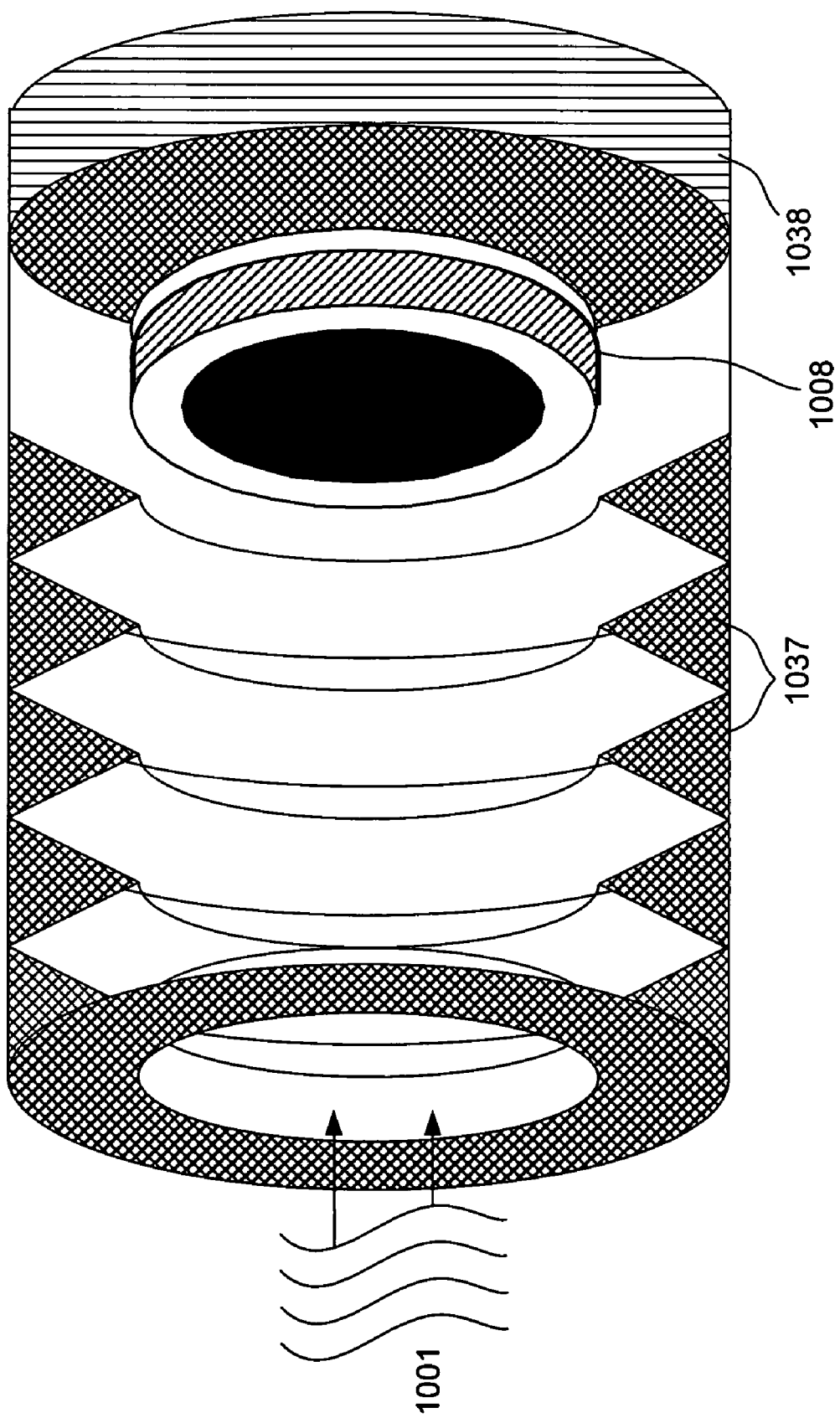
FIG. 10 is a pictorial diagram showing an embodiment of a sensor that includes an acoustical and/or electromagnetic absorbing material for noise reduction.

Referring to FIG. 10, a pictorial diagram illustrates an embodiment of a sensor that includes an acoustical and/or electromagnetic absorbing material for noise reduction. FIG. 10 depicts a sensor 1008 that utilizes a baffled material, such as a sound absorbing material 1037, an EM radiation absorbing baffled material, or a thermally shield material, or a combination thereof that can be used to block stray EM radiation, acoustic and thermal noise. In addition, an acoustic absorbing, a thermally insulating or an EM radiation shielding backing material 1038 can be placed behind the sensor 1008 to minimize noise. The sensor 1008 is mounted in a baffled sound and EM absorbing apparatus 1037 to reduce or minimize acoustic and EM noise. Optional acoustic damping material 1038 can be attached to the back of the sensor 1008 to minimize acoustic noise.

Figure 11:
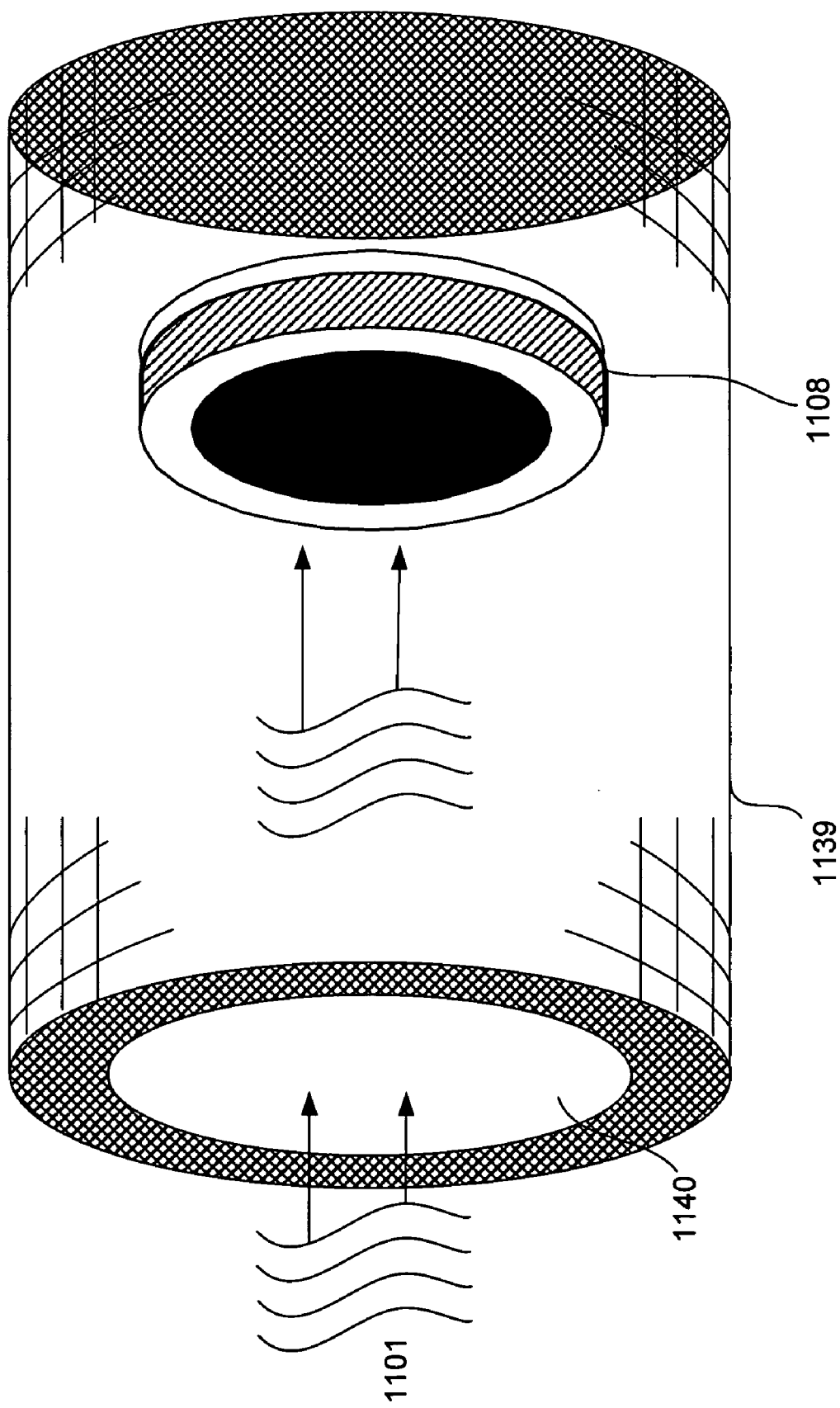
FIG. 11 is a pictorial diagram illustrating an embodiment of a sensor mounted in a vacuum chamber to minimize or reduce acoustic and thermal noise.

Referring to FIG. 11, a pictorial diagram illustrates an embodiment of a sensor that includes a vacuum chamber 1139 within which the sensor 1108 can be mounted. To further minimize noise, a sensor apparatus 1108 and some or all of the focusing optics can be mounted inside a vacuum chamber 1139 to minimize acoustic and thermal noise.

The sensor 1108 is mounted in a vacuum chamber 1139 to reduce or minimize acoustic and thermal noise. EM radiation enters the chamber through a window 1140 with the appropriate material that transmits the EM radiation in a given band. For multi-band imaging, multiple windows can be used, each designed for a particular wavelength band.

FIGS. 10 and 11 show structures that can be combined to further reduce or minimize noise by placing one chamber inside the other.

Figure 12A:
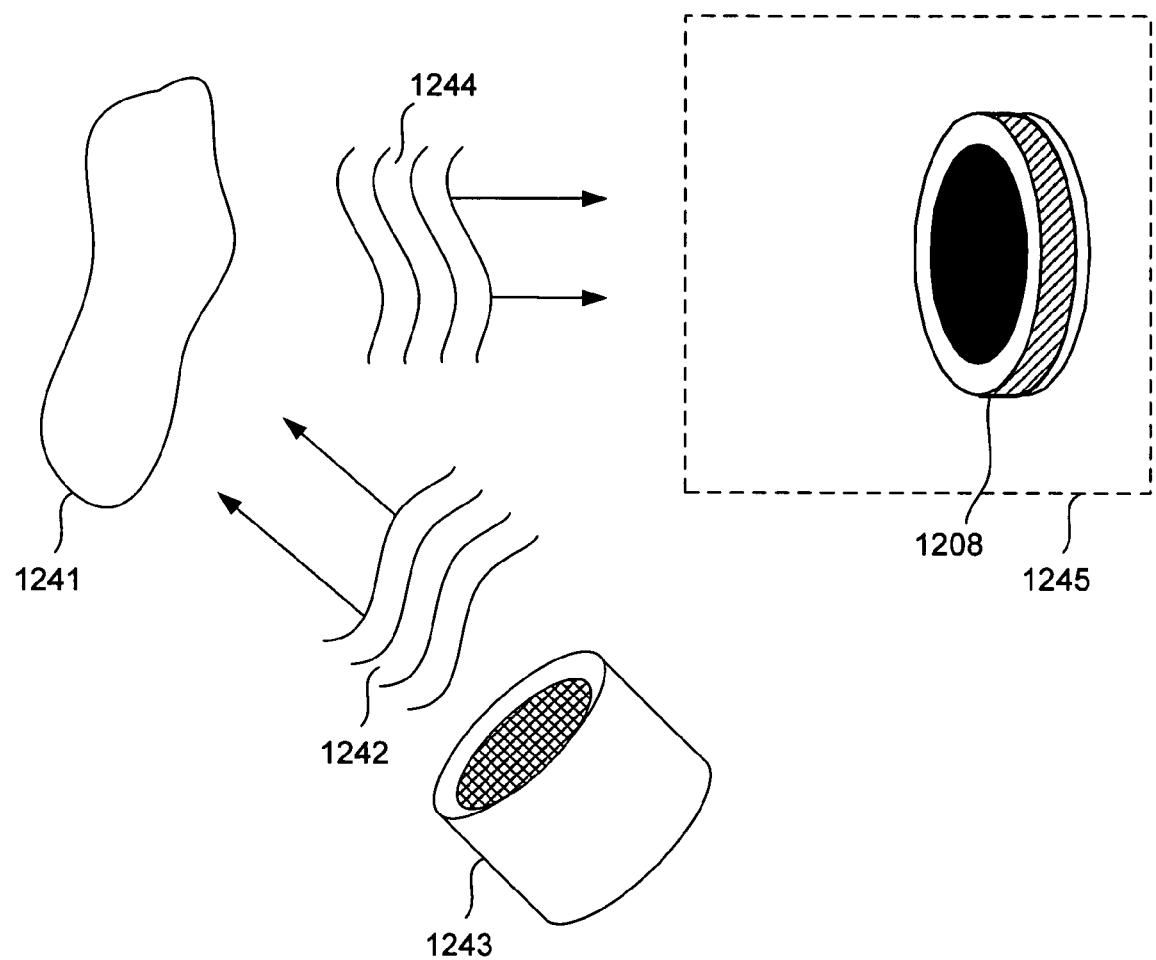
FIGS. 12A through 12C are schematic pictorial diagrams illustrating arrangements and embodiments that can be used for broadband imaging of objects.
Figure 12B:
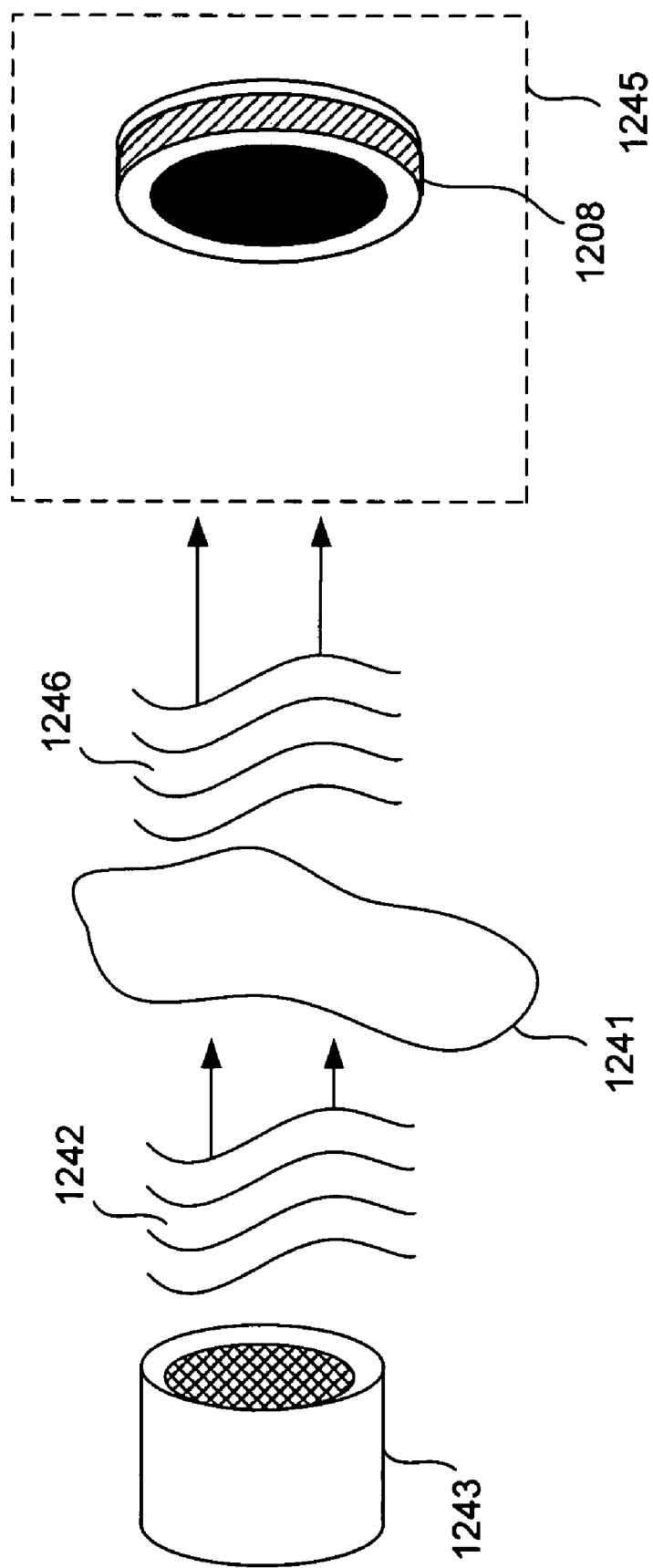
Figure 12C:
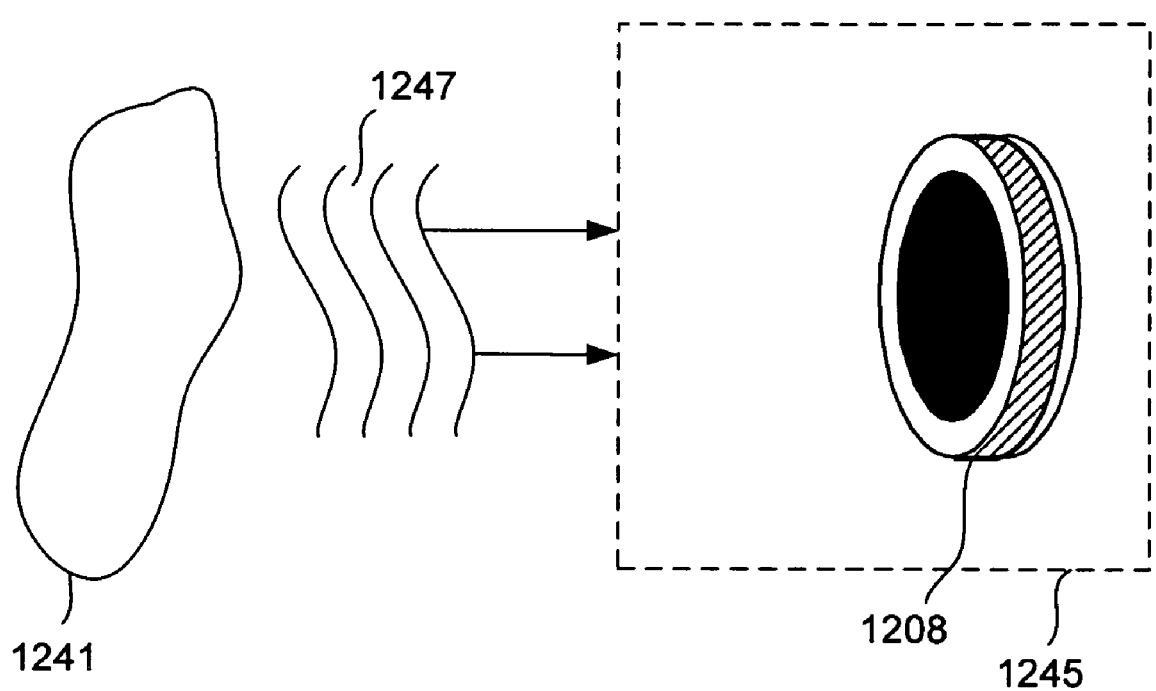

Referring to FIGS. 12A through 12C, schematic pictorial diagrams illustrate arrangements and embodiments that can be used for broadband imaging of objects. The various embodiments of broadband imaging sensors and sensing configurations can be used to image an arbitrary object either in reflection or a transmission mode as depicted in FIGS. 12A and 12B, respectively, or to image the object using the object's emitted EM field as depicted in FIG. 12C, such as a hot object or a radiating object.

FIG. 12A shows an example illustrating detection of an object 1241 with electromagnetic (EM) radiation 1242 incident on the object supplied either from a natural source, such as sun light, or a from an artificial source 1243, such as a laser, a light bulb, a thermal source, an X-ray, ultra-violet (UV), an infra-red, a Gamma-ray, a terahertz radiation, or any arbitrary EM radiation source. The incident radiation 1242 is reflected or scattered from the object 1241, or excites the object to emit a different wavelength than the incident wavelength. The reflected, scattered or the secondary emitted EM radiation 1244 travels towards the sensor 1208 combined with apparatus 1245, which is described relating to architectures depicted in FIGS. 1, 2, 8, and 9, and in some embodiments and configurations using either the pixelated methods depicted in FIGS. 3 and 4, or using moving slit or moving sensor methods depicted in FIG. 5, 6, or 7. The sensor 1208 contained in apparatus 1245 images the incident radiation 1244. In FIG. 12B, the object 1241 is detected in a transmission mode, where the incident EM radiation 1242 is transmitted through the object 1241, and the sensor apparatus detects the transmitted radiation 1246. In FIG. 12C, an example shows the object 2141 is the radiation source, emitting EM radiation 1247 which is captured by the sensor apparatus 1245. Example of emitted EM radiation is body heat, a hot object, or EM radiation from a radioactive material.

The various configurations and detection schemes shown in FIG. 12 can be used with any of the structures discussed herein throughout.

Referring to FIGS. 13A through 13D, several pictorial views illustrate embodiments and arrangements of sensors used for spectroscopic imaging. Narrow band imaging can be performed by combining the broadband single element or imaging sensors depicted herein with reflective, refractive, diffractive or transmission filter of the EM radiation.

Figure 13A:
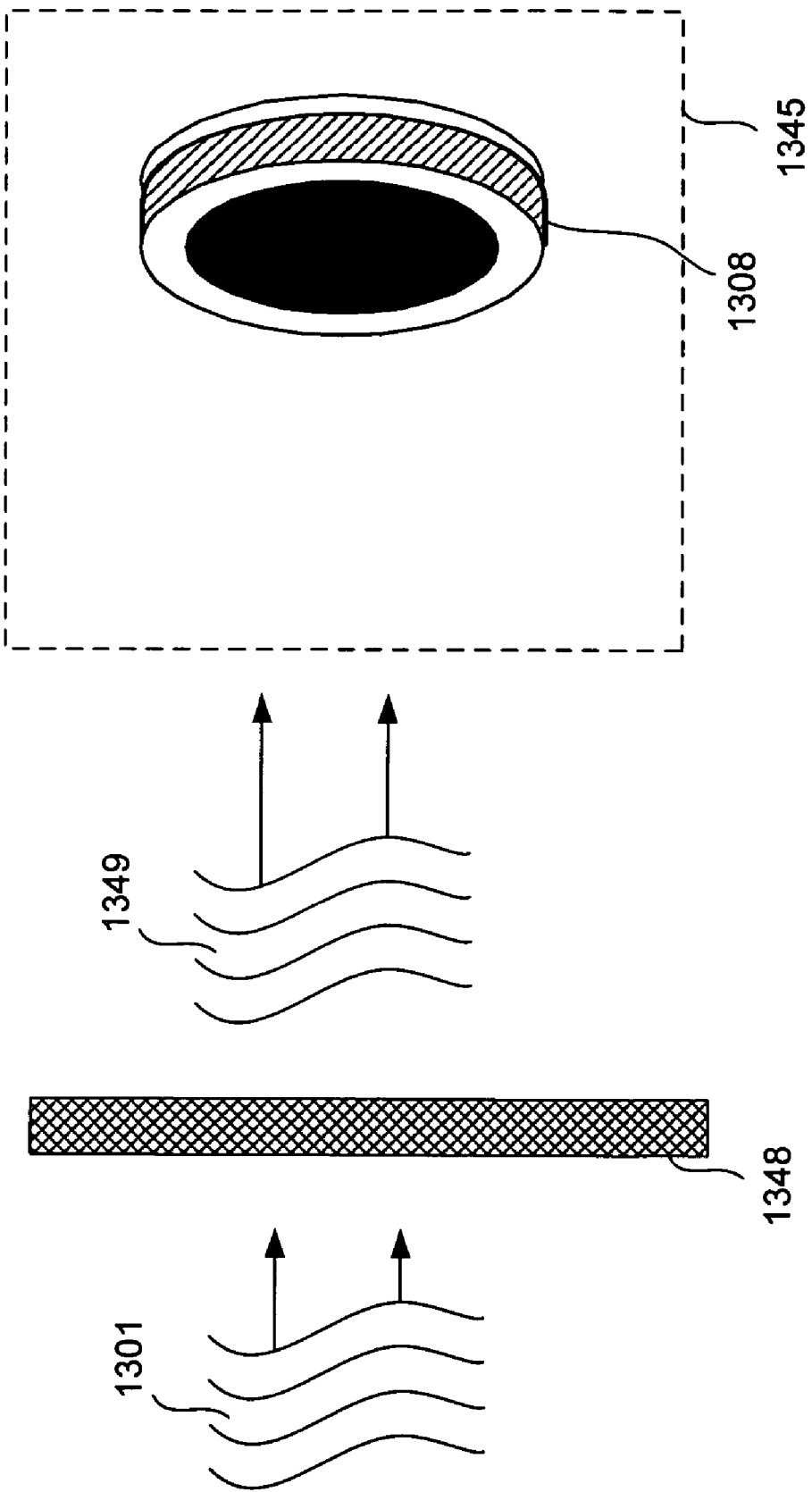
FIGS. 13A through 13D are several pictorial views illustrate embodiments and arrangements of sensors used for spectroscopic imaging.
Figure 13B:
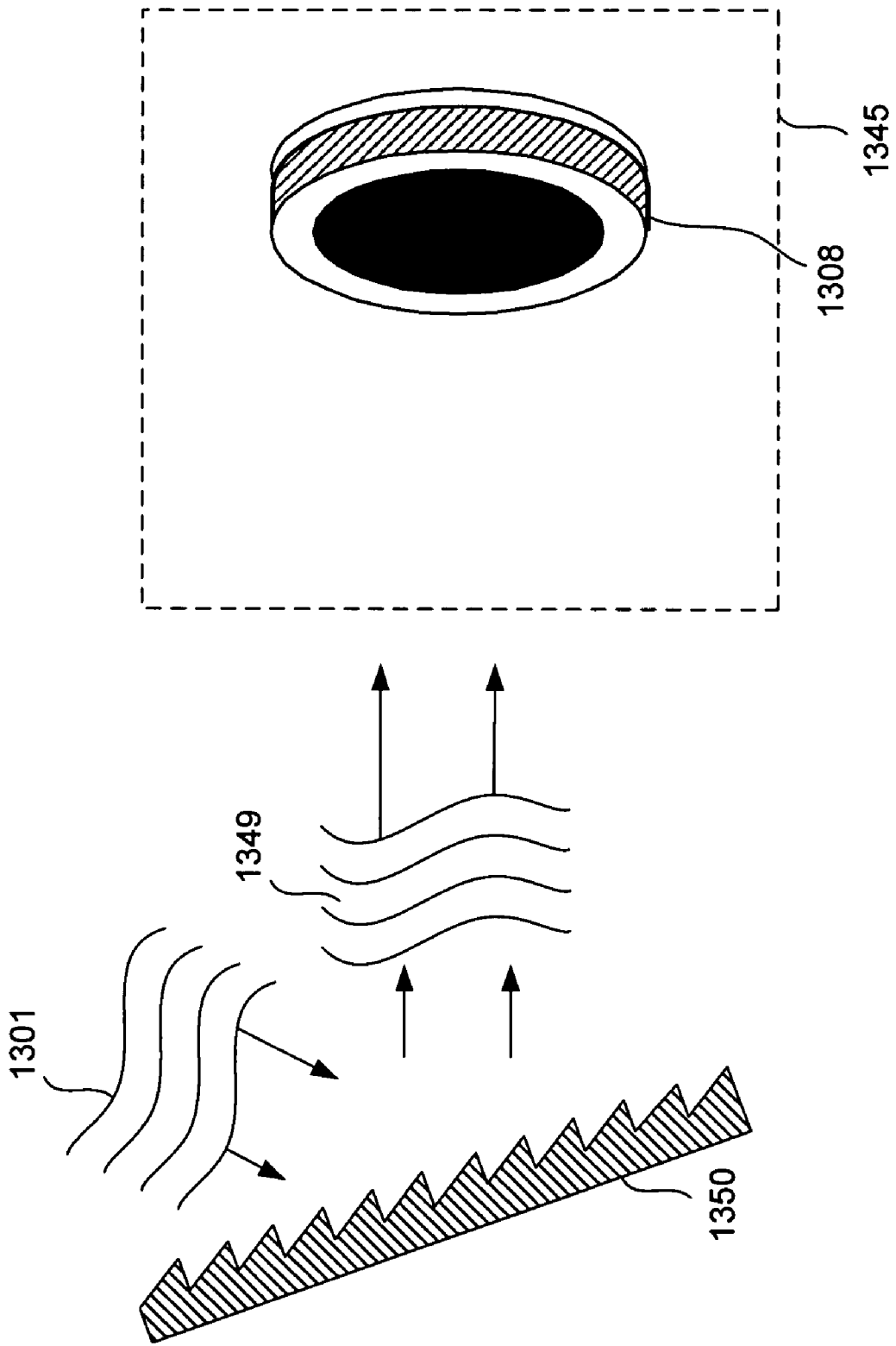
Figure 13C:
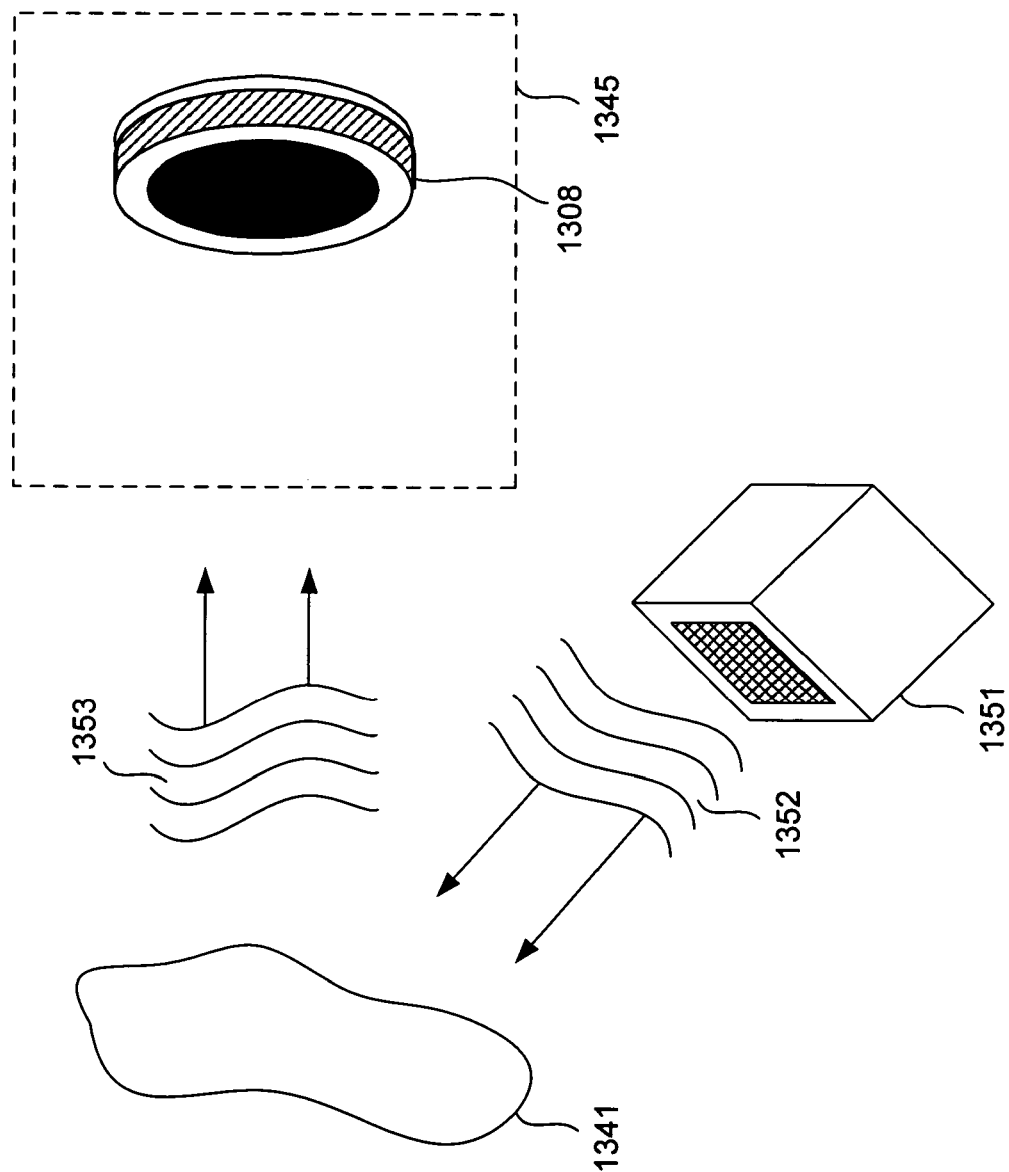
Figure 13D:
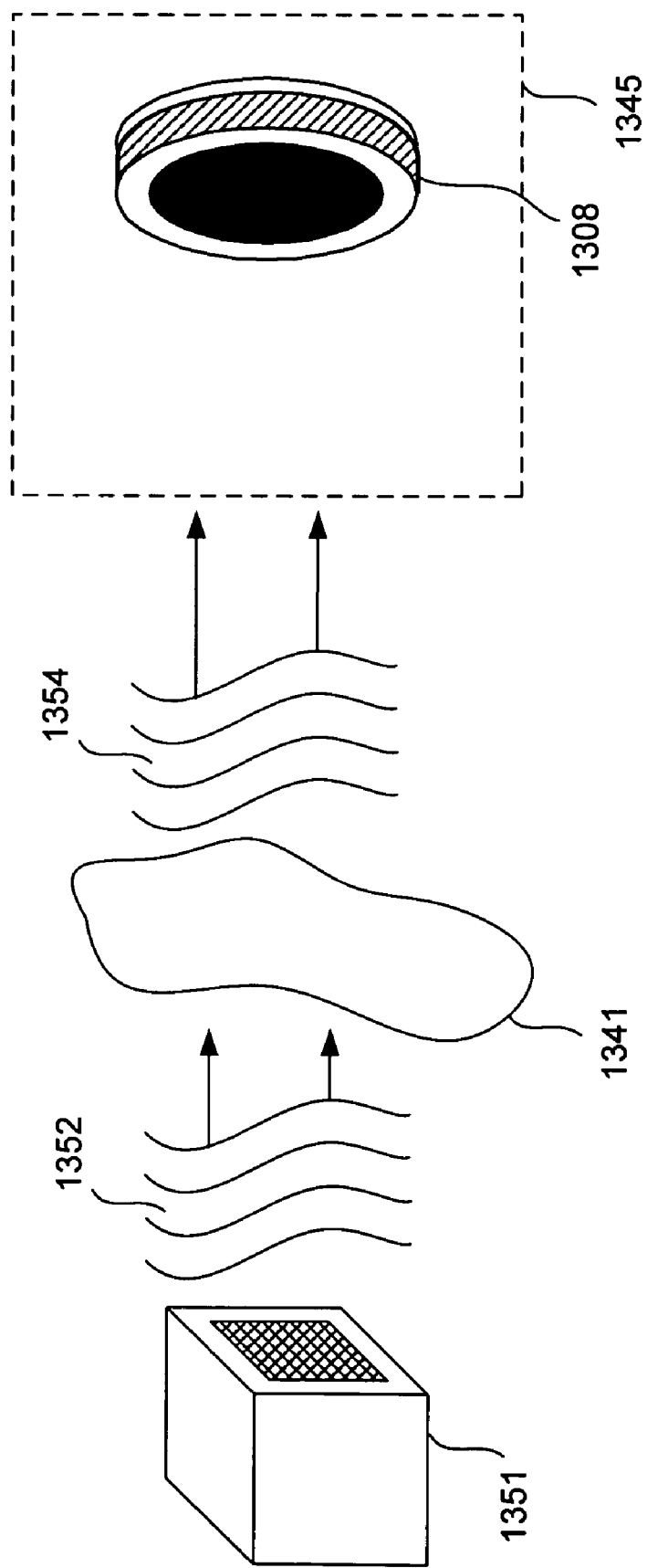

The illustrative sensors and detection devices are capable of obtaining a broadband image. In some applications, arrangements, and configurations decomposition of the broadband images to narrowband components is desired. More narrowband detection and sensing can be accomplished by several techniques. In one example technique, a variable filter can be inserted along the optical axis in front of the broadband imager as shown in FIG. 13A. In another technique, a ruled grating or a holographic or diffractive optical element can be used as shown in FIG. 13B. In a third technique, a narrowband EM source or a variable band EM source can be exploited as shown in FIGS. 13C and 13D.

The illustrative arrangements facilitate decomposition of a broadband image to narrowband regions. The configuration shown in FIG. 13A uses a narrowband fixed or a variable filter 1348 that only transmits part of the spectrum, resulting in a narrowband spectrum 1349. A filter 1348 is a variable filter or a fixed filter and can be either a narrowband filter, or a highpass or a low-pass wavelength filter. The arrangement shown in FIG. 13B implements a grating or a diffractive or a holographic optical element 1350 to diffract a narrow part of the broadband incident EM radiation 1301, resulting in a narrowband EM radiation 1349. Use of tunable wavelength EM radiation source 1351 that produces a narrowband EM radiation 1352 which can be used in a reflection mode is shown in FIG. 13C, resulting in a reflected or a stimulated spectrum 1353. The tunable wavelength EM radiation source 1351 can similarly be implemented in a transmission mode as shown in FIG. 13D. In the reflection mode, the incident radiation is reflected, scattered or results in a secondary emission 1353. In the transmission mode, the transmitted radiation 1354 is incident upon the sensor 1308.

The devices and arrangements depicted in FIGS. 13A through 13D produce a narrowband image and can be used to produce a spectroscopic image that decomposes a broadband spectrum to narrowband components. To achieve spectroscopic imaging using the arrangement shown in FIG. 13A, the filter 1348 can be changed, or a tunable filter can be used to tune the filter at a specific wavelength band. An image is captured using the imaging sensor apparatus 1345 and stored in electronic memory. The filter can be changed again or tuned to a different wavelength band, and another image taken which is also stored. Repeating the tuning, acquisition, and storage procedure produces multiple overlapping images that each contains a specific narrowband image. The combined images cover a broad spectral range. The procedure can also be implemented using the devices shown in FIGS. 13B through 13D. In the arrangement shown in FIG. 13B, the diffracted EM fields wavelength band can be tuned by rotating the angle of the grating or diffractive or holographic optical element 1350. In the configurations shown in FIGS. 13C and 13D, the radiation source 1351 can be tuned at a particular wavelength band, so that spectroscopic imaging is performed.

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims.

What is claimed is:

1. A sensor comprising:
a transducer substrate formed of a photo-acoustically sensitive material and having a receiving surface;
an absorptive layer coupled to the transducer substrate receiving surface that detects broad band electromagnetic (EM) radiation;
a first conductive layer coupling the absorptive layer to the transducer substrate; and
a second conductive layer coupled to the transducer substrate on a surface of the transducer substrate opposing the receiving surface.

2. The sensor according to claim 1 further:
the transducer substrate formed of a piezoelectric material.

3. The sensor according to claim 1 further comprising:
the transducer substrate formed of a capacitive material.

4. The sensor according to claim 1 further comprising:
a high-gain amplifier; and
the second conductive layer coupling the transducer substrate to the high-gain amplifier.

5. The sensor according to claim 1 further comprising:
imaging optics coupled to the transducer substrate configured for photo-acoustic imaging of incident electromagnetic (EM) radiation using spatial sampling, the imaging optics selected from a group consisting of broadband electromagnetic (EM) band-specific refractive lenses, diffractive optics, and broadband reflective mirrors.

6. The sensor according to claim 5 further comprising:
a read-only integrated circuit (ROIC);
a plurality of ROIC connectors coupled to the second conductive layer in an arrangement configured to patterning of the second conductive layer imaging picture elements (pixels); and
a third conductive layer coupling the ROIC connector plurality to the ROIC and patterned into a plurality of imaging picture elements (pixels).

7. The sensor according to claim 6 further comprising:
the transducer substrate patterned into a plurality of imaging picture elements (pixels).

8. The sensor according to claim 5 further comprising:
the transducer substrate patterned into a plurality of imaging picture elements (pixels).

9. The sensor according to claim 5 further comprising:
the second conductive layer patterned into a plurality of imaging picture elements (pixels) in a configuration adapted for imaging incident EM radiation.

10. The sensor according to claim 5 further comprising:
a plurality of patterned electrodes configured to selectively couple to the second conductive layer imaging picture element (pixel) plurality.

11. The sensor according to claim 5 further comprising:
a printed circuit board; and
a plurality of patterned conductive bumps on a first surface of the printed circuit board configured to selectively couple to the second conductive layer imaging picture element (pixel) plurality;
a plurality of electrodes located on a second surface of the printed circuit board opposite the first surface; and
a plurality of conductive patterned vias selectively coupling the conductive bump plurality to the electrode plurality.

12. A sensor comprising:
a transducer substrate formed of a photo-acoustically sensitive material and having a receiving surface;
an absorptive layer coupled to the transducer substrate receiving surface that detects broadband electromagnetic (EM) radiation; and
at least one diaphragm positioned between the transducer substrate and a source of incident electromagnetic (EM) radiation, the at least one diaphragm configured with at least one aperture enabling the incident EM radiation to pass to the transducer substrate; and
a scanner configured for coupling to the at least one diaphragm and spatially scanning incident EM radiation across the transducer substrate.

13. The sensor according to claim 12 further comprising:
two diaphragms each configured with a slit aperture with a dominant axis, the two diaphragms arranged consecutively in a pathway between the transducer substrate and the EM radiation source and having dominant axes arranged substantially perpendicular.

14. The sensor according to claim 12 further comprising:
a diaphragm configured with an iris or pinhole aperture.

15. The sensor according to claim 12 further comprising:
a shutter positioned between the transducer substrate and a source of incident electromagnetic (EM) radiation and configured to controllably block and pass the EM radiation.

16. The sensor according to claim 12 further comprising:
two diaphragms each configured with a slit aperture with a dominant axis, the two diaphragms arranged consecutively in a pathway between the transducer substrate and the EM radiation source and having dominant axes arranged substantially perpendicular; and
the scanner configured to move the two diaphragms mutually independently in scan speed and scan direction.

17. The sensor according to claim 16 further comprising:
the scanner configured to scan the two diaphragms in directions corresponding to the dominant axes.

18. A sensor comprising:
a transducer substrate formed of a photo-acoustically sensitive material and having a receiving surface;
an absorptive layer coupled to the transducer substrate receiving surface that detects broadband electromagnetic (EM) radiation; and
an electromagnetic (EM) radiation filter configured for insertion between the transducer substrate and a source of EM radiation that filters broadband response to a selected narrow band.

19. The sensor according to claim 1 further comprising:
at least one lens inserted between the transducer substrate and a source of electromagnetic (EM) radiation.

20. The sensor according to claim 1 further comprising:
at least one lens inserted between the transducer substrate and a source of electromagnetic (EM) radiation, the at least one lens selected from a group consisting of Fresnel lenses, diffractive optical elements, holographic optical elements, refractive optical elements, and specialty lenses.

21. The sensor according to claim 1 further comprising:
a high-gain amplifier;
the second conductive layer coupling the transducer substrate to the high-gain amplifier; and shielding containing the transducer substrate and grounding the high-gain amplifier.

22. The sensor according to claim 1 further comprising:
a high-gain amplifier;
the second conductive layer coupling the transducer substrate to the high-gain amplifier; and
a housing containing the transducer substrate and grounding the high-gain amplifier.

23. The sensor according to claim 22 further comprising:
an electrical filter coupled to the high-gain amplifier and adapted to filter electrical and acoustic noise within a selected frequency band.

24. The sensor according to claim 1 further comprising:
a housing containing the transducer substrate and formed of a baffled material selected from one or more materials of a group consisting of a sound absorbing material, an electromagnetic (EM) radiation absorbing material, a thermal shielding material.

25. The sensor according to claim 24 further comprising:
a backing material adapted to hold the transducer substrate within the housing and formed of a backing material selected from one or more materials of a group consisting of a sound absorbing material, an electromagnetic (EM) radiation absorbing material, a thermal shielding material.

26. The sensor according to claim 24 further comprising:
a vacuum chamber containing the transducer substrate and adapted to reduce acoustic and thermal noise.

27. The sensor according to claim 24 further comprising:
a vacuum chamber containing the housing and adapted to reduce acoustic and thermal noise.

28. A sensor comprising:
a piezoelectric substrate having a receiving surface;
an absorptive layer coupled to the substrate receiving surface that detects broadband electromagnetic (EM) radiation;
a first conductive layer coupling the absorptive layer to the piezoelectric substrate; and
a second conductive lever coupled to the piezoelectric substrate on a surface of the piezoelectric substrate opposing the receiving surface.

29. The sensor according to claim 28 further comprising:
a read-only integrated circuit (ROIC);
a plurality of ROIC connectors coupled to the second conductive layer in an arrangement configured to patterning of the second conductive layer imaging picture elements (pixels); and
a third conductive layer coupling the ROIC connector plurality to the ROIC and patterned into a plurality of imaging picture elements (pixels).

30. The sensor according to claim 29 further comprising:
the piezoelectric substrate patterned into a plurality of imaging picture elements (pixels).

31. The sensor according to claim 28 further comprising:
the piezoelectric substrate patterned into a plurality of imaging picture elements (pixels).

32. The sensor according to claim 28 further comprising:
a high-gain amplifier;
the second conductive layer coupling the piezoelectric substrate to the high-gain amplifier; and
a metallic housing containing the piezoelectric substrate and grounding the high-gain amplifier.

33. The sensor according to claim 32 further comprising:
acoustic shielding around the piezoelectric substrate within the metallic housing.

34. A sensor comprising:
a transducer substrate formed of a capacitive material and having a receiving surface;
an absorptive layer coupled to the transducer substrate receiving surface that detects broadband electromagnetic (EM) radiation;
a first conductive layer coupling the absorptive layer to the transducer substrate; and
a second conductive lever coupled to the transducer substrate on a surface of the transducer substrate opposing the receiving surface, the second conductive layer patterned into a plurality of imaging picture elements (pixels).

35. The sensor according to claim 34 further comprising:
a read-only integrated circuit (ROIC);
a plurality of ROIC connectors coupled to the second conductive layer in an arrangement configured to patterning of the second conductive layer imaging picture elements (pixels); and
a third conductive layer coupling the ROIC connector plurality to the ROIC and patterned into a plurality of imaging picture elements (pixels).

36. The sensor according to claim 35 further comprising:
the transducer substrate patterned into a plurality of imaging picture elements (pixels).

37. The sensor according to claim 34 further comprising:
the transducer substrate patterned into a plurality of imaging picture elements (pixels).

38. A method of acquiring subsurface structural information comprising:
detecting broadband electromagnetic (EM) radiation incident at a receiving surface of a transducer substrate formed of a photo-acoustically sensitive material and coated by an absorptive layer; and
positioning the transducer substrate relative to a radiating object in a configuration to receive the incident EM radiation.

39. The method according to claim 38 further comprising:
generating electromagnetic (EM) radiation from the radiating object by generation selected from a group consisting of reflecting or scattering radiation from the object using a radiation source, transmitting radiation through the object using a radiation source, and emitting radiation from the object.

40. The method according to claim 38 further comprising:
decomposing the broadband electromagnetic (EM) radiation into narrowband components by decomposition selected from a group consisting of inserting a variable filter between the radiating object and the transducer substrate, inserting a ruled grating between the radiating object and the transducer, inserting a holographic optical element between the radiating object and the transducer substrate, inserting a diffractive optical element between the radiating object and the transducer substrate, irradiating the radiating object using a narrowband EM source, and irradiating the radiating object using a variable band EM source.

* * * * *